United States Patent
Segman

(10) Patent No.: US 8,489,165 B2
(45) Date of Patent: Jul. 16, 2013

(54) FINGER DEPLOYED DEVICE FOR MEASURING BLOOD AND PHYSIOLOGICAL CHARACTERISTICS

(75) Inventor: Yosef Segman, Zichron Yaakov (IL)

(73) Assignee: Cnoga Medical Ltd., Or Akiva (IL)

( * ) Notice: Subject to any disclaimer, the term of this patent is extended or adjusted under 35 U.S.C. 154(b) by 1295 days.

(21) Appl. No.: 12/260,251

(22) Filed: Oct. 29, 2008

(65) Prior Publication Data
US 2010/0105996 A1   Apr. 29, 2010

(51) Int. Cl.
*A61B 5/00* (2006.01)

(52) U.S. Cl.
USPC .......................................... 600/323; 600/331

(58) Field of Classification Search
USPC ................. 600/344, 310, 309, 316, 331, 323
See application file for complete search history.

(56) References Cited

U.S. PATENT DOCUMENTS

| | | | |
|---|---|---|---|
| 4,981,355 A * | 1/1991 | Higgins | 356/243.1 |
| 5,490,523 A * | 2/1996 | Isaacson et al. | 600/323 |
| 6,873,865 B2 * | 3/2005 | Steuer et al. | 600/322 |
| 7,239,905 B2 * | 7/2007 | Kiani-Azarbayjany et al. | 600/316 |
| 2006/0211922 A1 * | 9/2006 | Al-Ali et al. | 600/310 |

* cited by examiner

*Primary Examiner* — Max Hindenburg
(74) *Attorney, Agent, or Firm* — Mark M. Friedman

(57) ABSTRACT

The present invention relates to a device for measuring blood and physiological characteristics by passing light through human tissue that is configured for deployment on a human finger. The device includes a lower finger-trough configured in the main housing of the device; a hingedly attached closeable lid that has an upper finger-trough configured for deployment of at least one finger stabilizing element, the lid being latchable in a closed position; a finger stabilizing element made of a material having flexibly soft malleable characteristics so as to sealingly engage the top of the finger; a light source that is deployed in the sloped end wall of the lower finger-trough adjacent to the lower portion of the finger tip; and an end cap the is deployable on the open end of the device when the lid is in the closed position, which enables calibration of the device with a minimum of light wave "noise" from ambient light.

4 Claims, 12 Drawing Sheets

FINGER DEPLOYED DEVICE FOR MEASURING BLOOD AND PHYSIOLOGICAL CHARACTERISTICS

FIELD AND BACKGROUND OF THE INVENTION

The present invention relates to devices for measuring blood and physiological characteristics by passing light through human tissue and, in particular, it concerns a device configured for deployment on a human finger.

It is known to measure certain blood and physiological characteristics, such as oxygen, glucose and $CO^2$ levels as well as pH, blood pressure, hemoglobin, hematocrit, blood viscosity, bilirubin, blood pigmentation, heart rate, heart rate distortion and blood pressure distortion, by passing light through tissues that include blood vessels. However, actual deployment of such devices on the patient provide a number of heretofore unresolved issues such as freedom of movement and introduction of light wave "noise" from the ambient light into the sensor.

There is therefore a need for a device for measuring blood and physiological characteristics by passing light through a human finger that is securely attachable to the finger and lessens, if not eliminates, light wave "noise".

SUMMARY OF THE INVENTION

The present invention is a device for measuring blood and physiological characteristics by passing light through human tissue that is configured for deployment on a human finger.

According to the teachings of the present invention there is provided, a device for measuring blood and physiological characteristics, the device configured for deployment on a finger, the device comprising: (a) a main housing having a lower finger-trough configured to engage the bottom side of the finger, the lower finger-trough having an open end, a closed end and having cross-sectional contours that are complimentary to a bottom side of the finger; (b) a closeable lid having an upper finger-trough having an open end and a closed end that corresponds to the lower finger-trough, the lid being hingedly attached to the main housing and latchable in a closed position; (c) at least one finger stabilizing element configured for deployment in the upper finger-trough and configured to engage a top side of the finger; (d) at least one light source deployed on the sloped closed end of the lower finger-trough; (e) at least one light sensor opening configured in a bottom surface of the lower finger-trough; and (f) an end cap configured for deployment on the device when the lid is in a closed position so as to substantially close the open ends of the upper and lower finger-troughs.

According to a further teaching of the present invention, there is also provided (g) a readout display unit deployed on the main housing so as to be adjacent to a palm of a hand of a patient during use.

There is also provided according to the teachings of the present invention, a main housing for a device for measuring blood and physiological characteristics, the device configured for deployment on a finger, the main housing comprising a lower finger-trough configured to engage the bottom side of the finger, the lower finger-trough having an open end, a closed end and having cross-sectional contours that are substantially complimentary to a bottom side of the finger such that a wall of the closed end is sloped so as to substantially correspond to a tip of the finger.

According to a further teaching of the present invention, the lower finger-trough is configured for engagement with at least a portion of a finger stabilizing element deployed in a lid of the device so as to substantially enclose the finger when the lid is deployed in a closed position.

There is also provided according to the teachings of the present invention, a closeable lid for device for measuring blood and physiological characteristics, the device configured for deployment on a finger, the closeable lid comprising: an upper finger-trough having an open end and a closed end, the lid being hingedly attached to a main housing and latchable in a closed position.

According to a further teaching of the present invention, the hinged attachment is such that the lid rotates about an axis that is parallel to the length of the finger.

According to a further teaching of the present invention, the upper finger-trough is configured to accept deployment of at least one finger stabilizing element configured to engage a top side of the finger.

There is also provided according to the teachings of the present invention, a finger stabilizing element for stabilizing the position of a finger in a device for measuring blood and physiological characteristics by passing light through at least a portion of a human finger, the finger stabilizing element comprising: (a) at least first surface configured for engaging the device for measuring blood and physiological characteristics; and (b) at least a second surface configured for engaging a top side of at least a portion of the finger, the second surface including a finger engagement trough having cross-sectional contours that are substantially complimentary to the top side of the finger becoming narrower and shallower toward the end of the finger engagement trough which substantially corresponds to a tip of the finger; wherein the finger stabilizing element is configured from a material having flexibly soft malleable characteristics so as to sealingly engage the finger and thereby at least lessen an amount of ambient light noise entering the device.

According to a further teaching of the present invention, the cross-sectional contour that is substantially complimentary to the top side of the finger becomes narrower and shallower in a substantially continuous slope.

According to a further teaching of the present invention, the cross-sectional contour that is substantially complimentary to the top side of the finger becomes narrower and shallower along a slope that varies along its length.

According to a further teaching of the present invention, the variance in the slope is in stepped increments.

According to a further teaching of the present invention, the first surface is configured to engage at least a portion of an upper finger trough configured in a lid of the device for measuring blood and physiological characteristics.

According to a further teaching of the present invention, there is also provided a region configured to engage at least a portion of a corresponding lower finger trough configured in a main body of the device for measuring blood and physiological characteristics when the lid is in a closed position.

According to a further teaching of the present invention, there is also provided a plurality of interchangeable elements each having a different sized the finger engagement trough corresponding to different sized human fingers.

According to a further teaching of the present invention, there is also provided a plurality of nesting elements each having a different sized the finger engagement trough corresponding to different sized human fingers wherein the first surface of each nesting element is configured to attachably engage the second surface of a next element in the nesting sequence.

According to a further teaching of the present invention, the flexibly soft malleable characteristics are such that the finger stabilizing element reshapes to conform to at least a size and a shape of the finger when the device is deployed on the finger.

There is also provided according to the teachings of the present invention, a device for measuring blood and physiological characteristics, the device configured for deployment on a finger, the device comprising: (a) at least one light source deployed on a sloped wall of a closed end of a lower finger-trough; and (b) at least one light sensor opening configured in a bottom surface of the lower finger-trough; wherein light enters a tip of the finger is an area just below the nail and at least a portion of the light exits the finger in a area in the bottom of the finger before the first knuckle, thereby entering the light sensor opening.

According to a further teaching of the present invention, an opening for the light source and the light sensor opening are each configured with a raised lip circumscribing each of the opening for the light source and the light sensor opening, so as to enhance contact with the surface of the finger.

According to a further teaching of the present invention, the at least one light source is configured as an array of light sources.

According to a further teaching of the present invention, light emitted by the at least one light sources is directed through at least one light source opening.

According to a further teaching of the present invention, the emitted by the at least one light sources is directed to the at least one light source opening by a light tunnel arrangement.

There is also provided according to the teachings of the present invention, a device for measuring blood and physiological characteristics, the device configured for deployment on a finger, the device comprising: (a) a main housing having a lower finger-trough configured to engage the bottom side of the finger, the lower finger-trough having an open end; (b) a closeable lid having an upper finger-trough having an open end that corresponds to the lower finger-trough; and (c) an end cap configured for deployment on the device when the lid is in a closed position; wherein the end cap substantially seals the open ends of the upper and lower finger-troughs such that ambient light is unable to enter an interior volume defined by the lower and upper finger-troughs and the end cap.

According to a further teaching of the present invention, there is also provided a system for passing light through at least a portion of a human finger so as to measure blood and physiological characteristics, wherein the sealing of the open ends of the upper and lower finger-troughs enables calibration of the system.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a device for measuring blood and physiological characteristics by passing light through human tissue that is configured for deployment on a human finger. The blood and physiological characteristics measured by the present invention may include, by non-limiting example, oxygen, glucose and $CO^2$ levels as well as pH, blood pressure, hemoglobin, hematocrit, blood viscosity, bilirubin, blood pigmentation, heart rate, heart rate distortion and blood pressure distortion.

The principles and operation of a device for measuring blood and physiological characteristics according to the present invention may be better understood with reference to the drawings and the accompanying description.

By way of introduction, the present invention relates to a device for measuring blood and physiological characteristics by passing light through human tissue that is configured for deployment on a human finger wherein the device includes a number of novel features which can be used individually to benefit and when combined provide a unique synergy.

These features include:
1. A uniquely shaped lower finger-trough configured in the main housing of the device, which will be discussed in detail with regard to FIGS. 1-5.
2. A hingedly attached closeable lid that has an upper finger-trough configured for deployment of at least one finger stabilizing element, the lid being hinged at the side and latchable in a closed position, which will be discussed in detail with regard to FIGS. 1, 4, 5 and 6.
3. A finger stabilizing element made of a material having flexibly soft malleable characteristics so as to sealingly engage the top of the finger and at least partially conform to the shape of the finger so as to at least lessen an amount of ambient light noise entering the device as will be discussed in detail with regard to FIGS. 1 and 4-8.
4. A light source that is deployed in the sloped end wall of the lower finger-trough adjacent to the lower portion of the finger tip, as will be discussed with regard to FIGS. 2 and 3.
5. An end cap is deployable on the open end of the device when the lid is in the closed position, which enables calibration of the device with a minimum of light wave "noise" from ambient light, which will be discussed in detail with regard to FIGS. 8 and 9.

Figure 1:
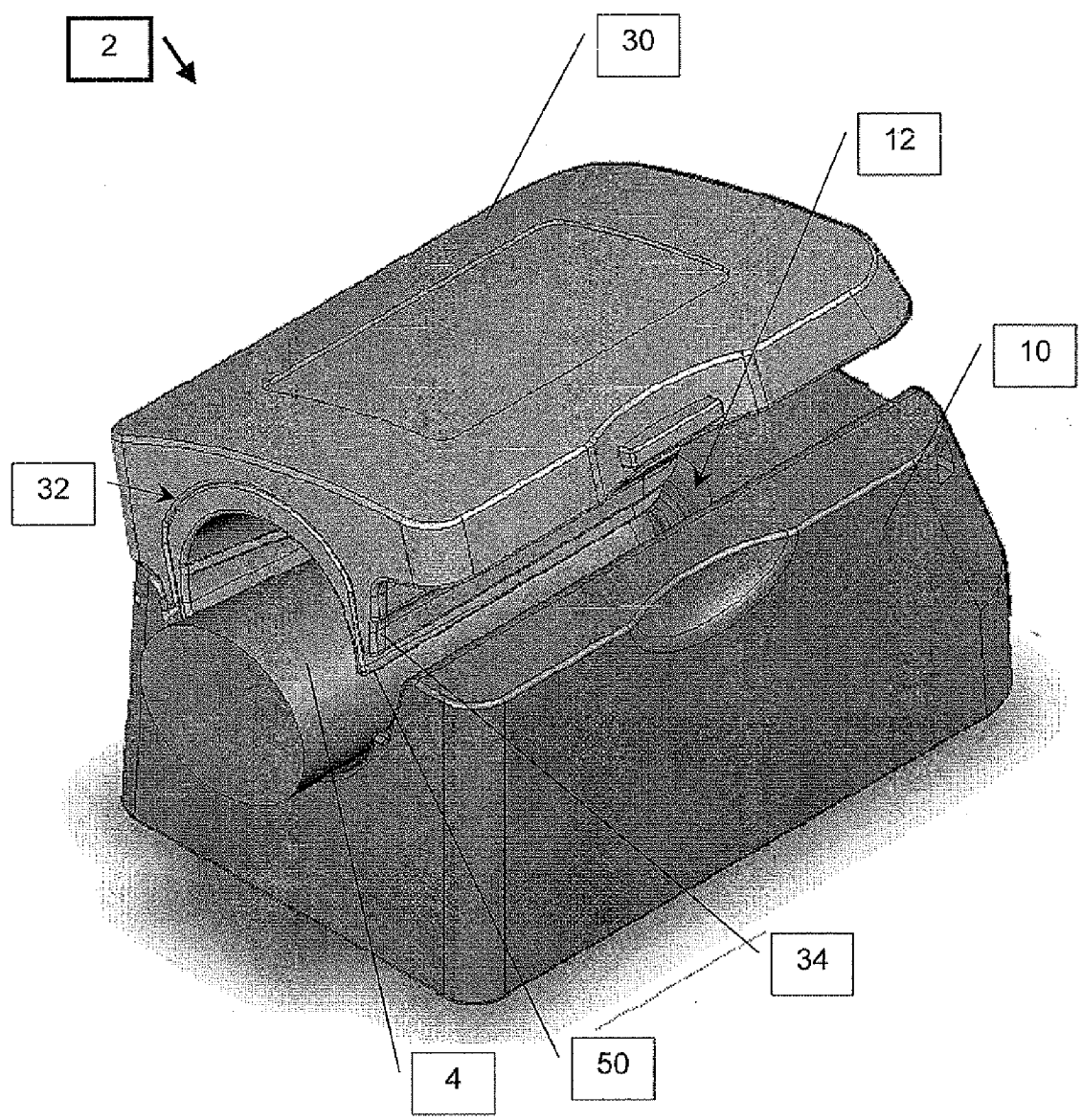
FIG. 1 is an isometric view of a device for measuring blood and physiological characteristics by passing light through human tissue, constructed and operational according to the teachings of the present invention.

Referring now to the drawings, FIG. 1 illustrates a device 2 for measuring blood and physiological characteristics by passing light through human tissue that is configured for deployment on a human finger 4 that incorporates the above listed features. Visible here are, the uniquely shaped lower finger-trough 12 configured in the main housing 10, the hingedly attached closeable lid 30 that has an upper finger-trough 32 configured for deployment of at least one finger stabilizing element 50, and the finger stabilizing element that sealingly engages the top of the finger 4.

Figure 2:
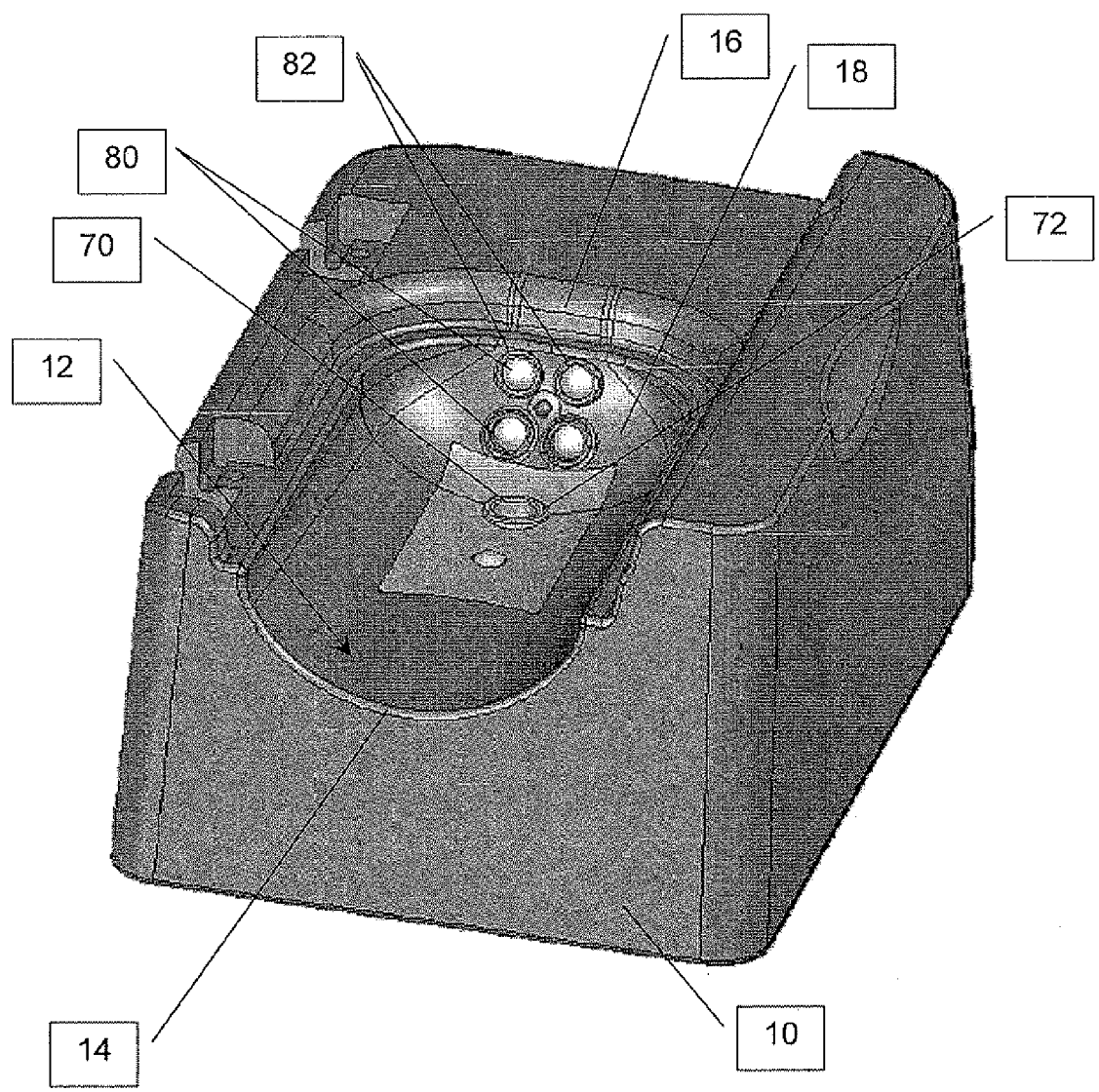
FIGS. 2 and 3 are isometric views of the main housing of the embodiment of FIG. 1.
Figure 3:
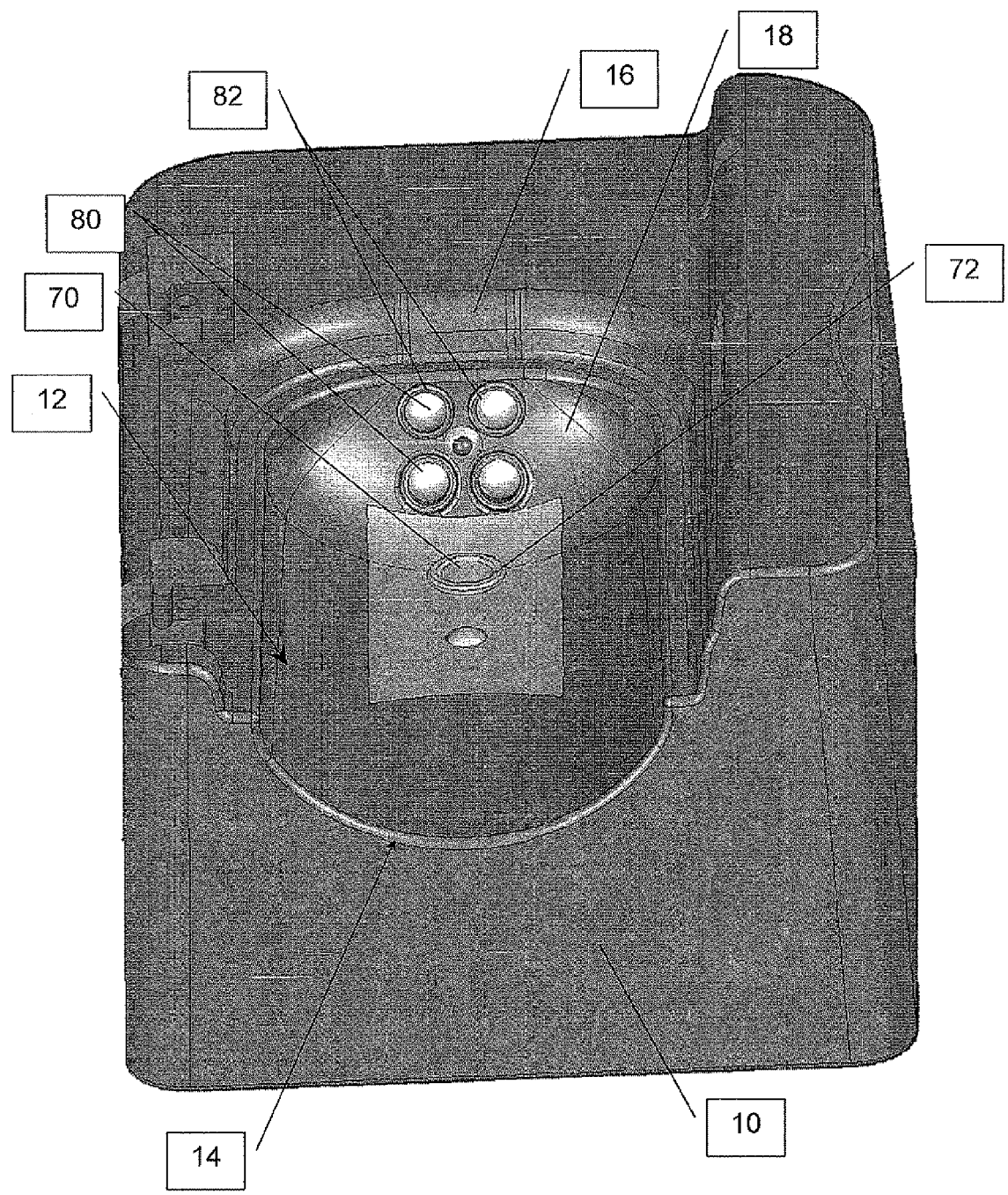
Figure 4:
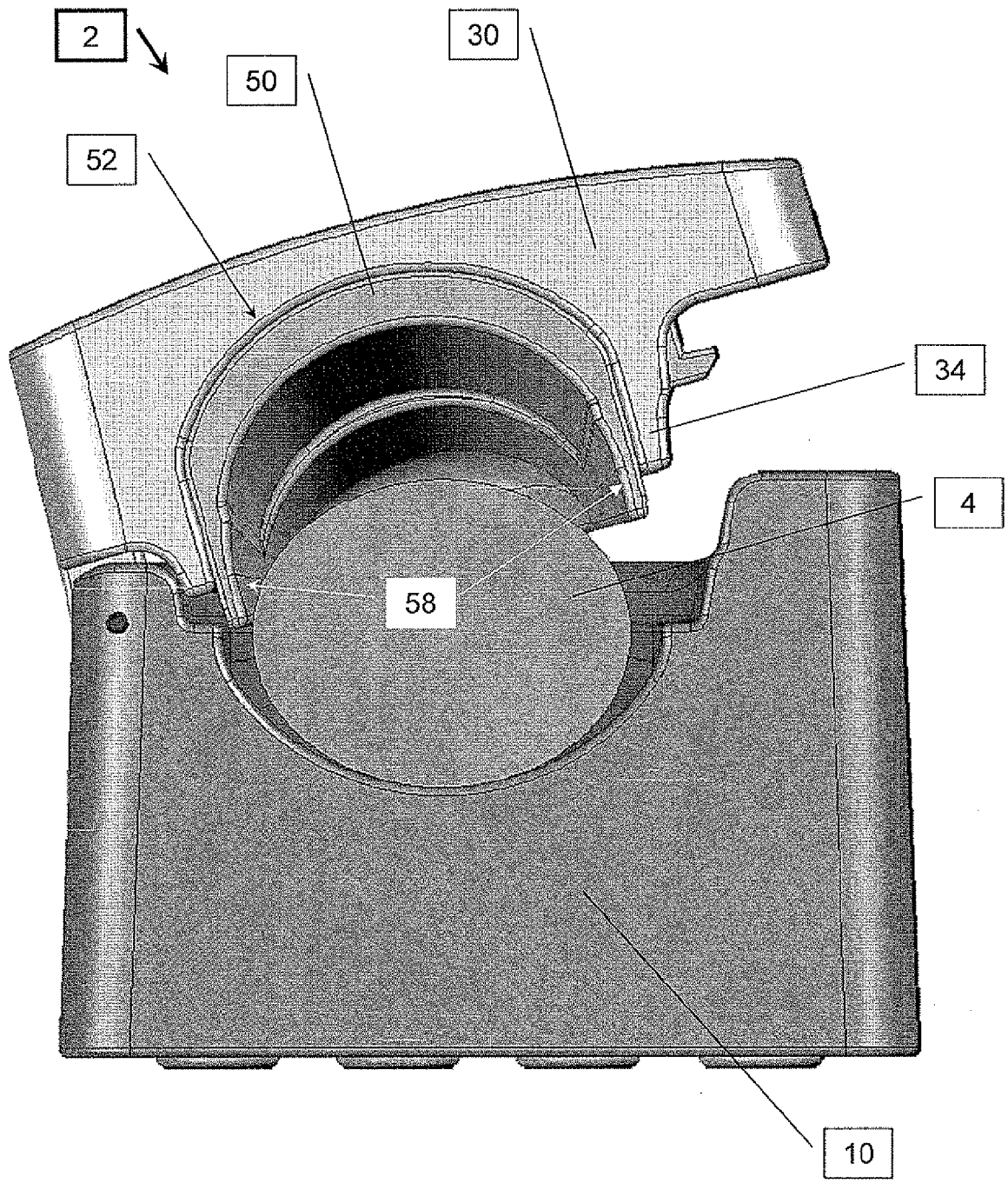
FIG. 4 is an end view of the embodiment of FIG. 1, with the lid in an open position.

As illustrated herein, the main housing 10 includes a lower finger-trough 12 that is configured to engage the bottom side of the finger 4. As best illustrated in FIGS. 2 and 3, the lower finger-trough has an open end 14 and a closed end 16. The cross-sectional contours of tie lower finger-trough 12 are substantially complimentary to the bottom side of the finger 4. As such, the wall 18 of the closed end 16 is sloped so as to substantially correspond to the curvature of the tip of human finger 4. Preferably, the bottom of the lower finger-trough 12 is also sloped such that the lower finger-trough 12 becomes shallower toward the closed end 16.

Closeable lid 30 is hingedly attached to the side of the main housing 10 so as to rotate about an axis that is parallel to the length of the finger 4. Further, the lid is configured to latchingly engage the main housing 10 when in a closed position. This enables the device 2 to be securely deployed on the finger 4 of a human patient. This secure deployment allows the finger and even the hand to move without impacting the ability of the device to perform the required measurements, thereby eliminating the need for medical staff to closely monitor, and possibly control, patient movement during testing.

Figure 5:
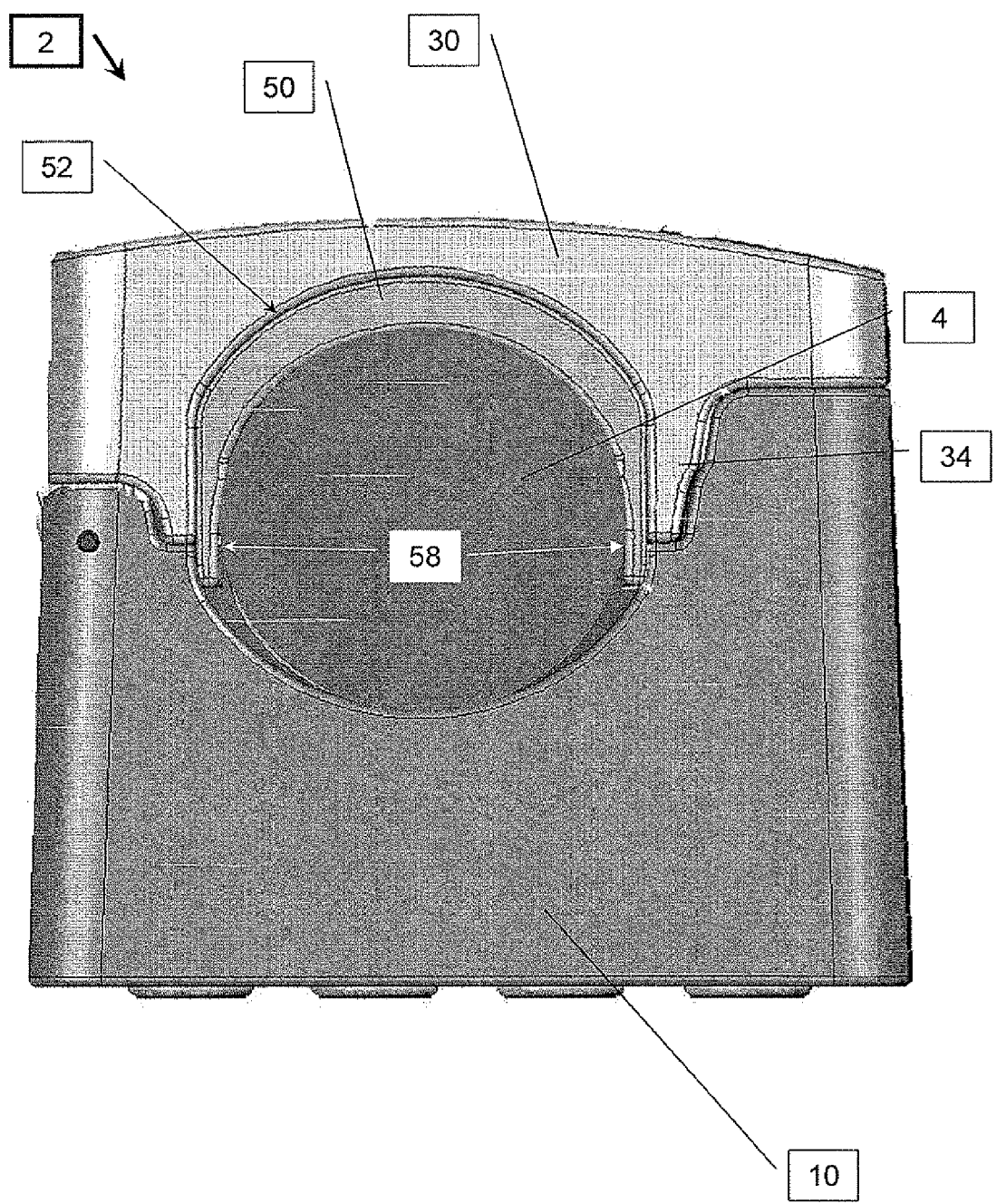
FIG. 5 is an end view of the embodiment of FIG. 1, with the lid in a closed position.

As illustrated in FIG. 5, the top edge of the lower finger trough 12 is configured to accept insertion of a rim portion 34 of the lid 30 as well as a region along the lower edge 58 of the finger stabilizing element 50, which is deployed in the upper finger-trough 32 in the lid 30. Such a sealing engagement of the finger 4 assists in preventing ambient light from reaching the light sensor opening 70 configured in a bottom surface of the lower finger-trough 14.

The finger stabilizing element 50, is configured for stabilizing the position of the finger 4 against the light source 80 deployed on a sloped wall 18 of the closed end 16 of a lower finger-trough 12 and the light sensor opening 70 configured in a bottom surface of said lower finger-trough 12, as well sealingly engaging the finger 4.

Figure 7:
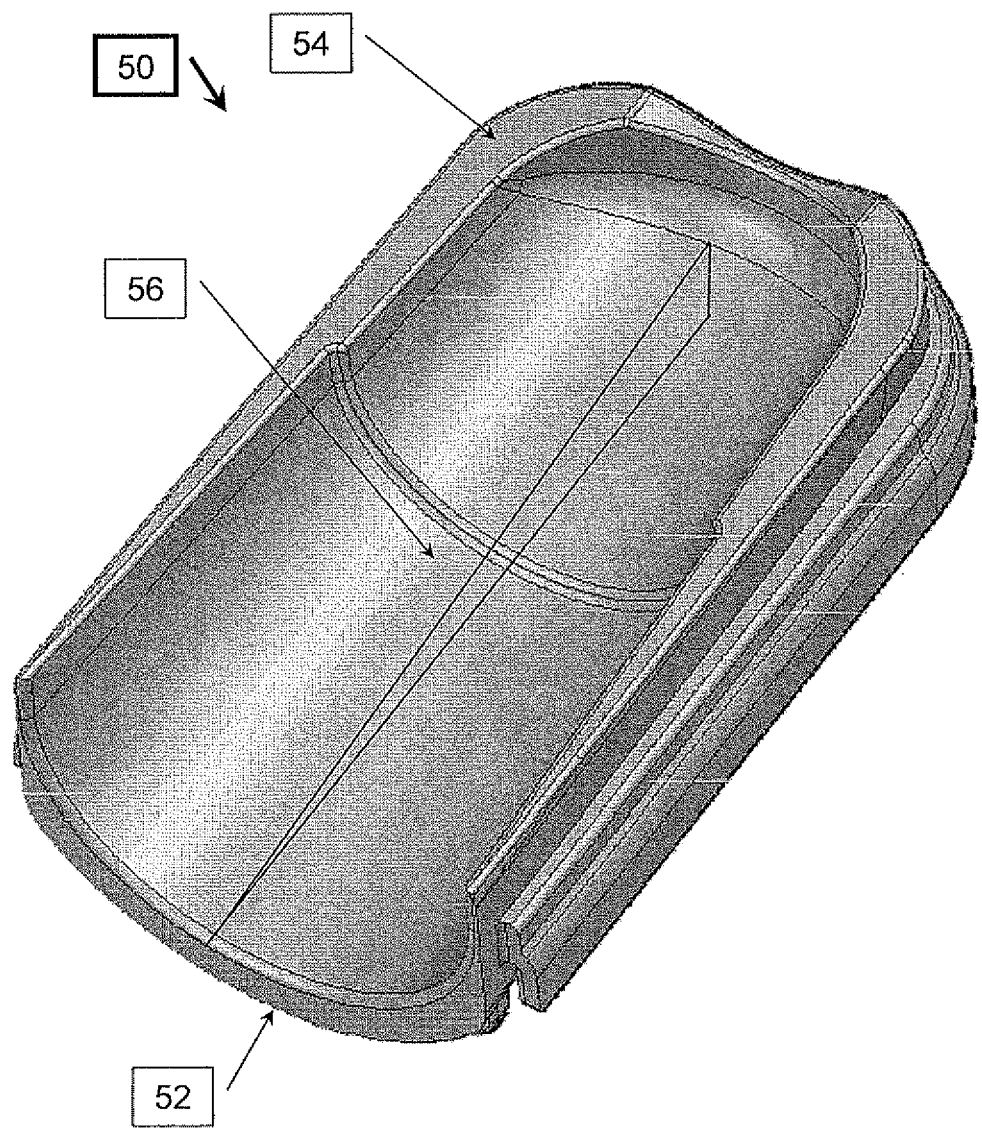
FIG. 7 is an isometric view of a single finger stabilizing element constructed and operational according to the teachings of the present invention.
Figure 8:
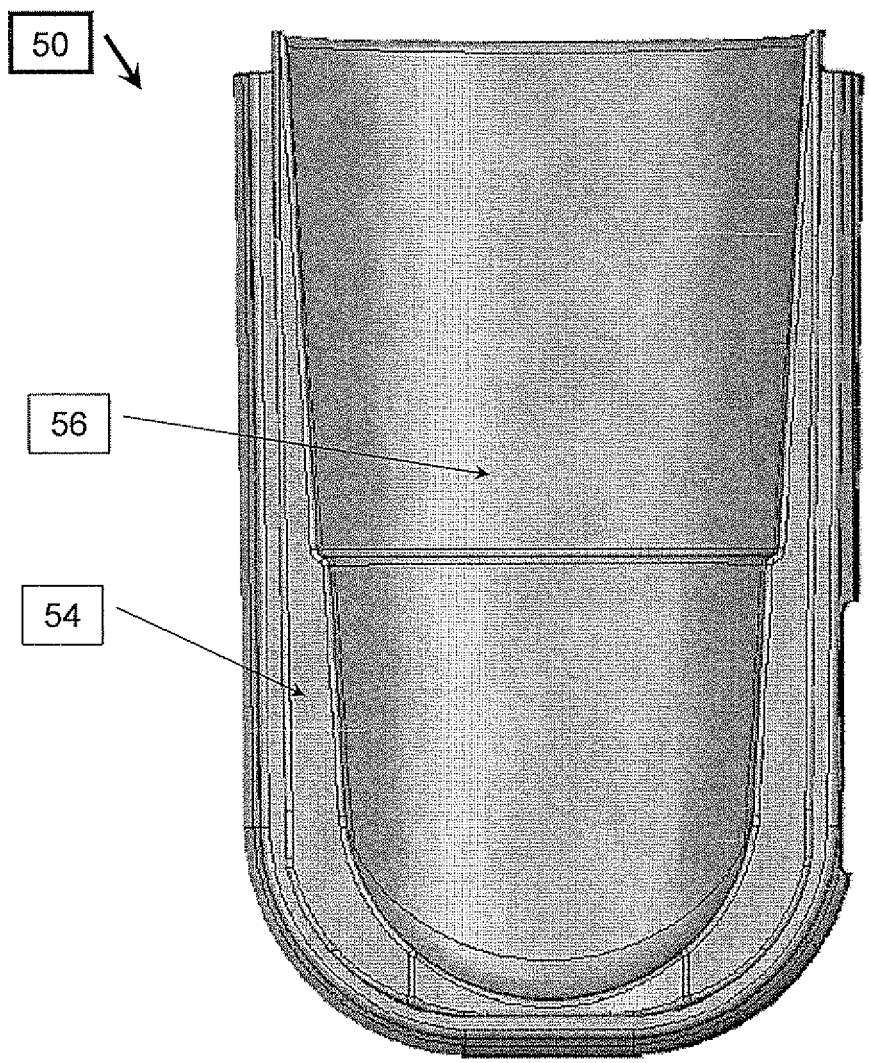
FIG. 8 is a top view of the embodiment of FIG. 7.

As seen best in FIGS. 7 and 8, the finger stabilizing element 50, includes at least a first surface 52 configured for attachably engaging the upper finger-trough 32 configured in the lid 30. It will be appreciated that finger stabilizing element 50 may be implemented as a single use disposable element.

The finger stabilizing element 50, also includes at least a second surface 54 configured for engaging the top side of at least a portion of the finger 4. The second surface 54 includes a finger engagement trough 56 having cross-sectional contours that are substantially complimentary to the top side of the finger 4 becoming narrower and shallower toward the end of the finger engagement trough 54 so as to substantially correspond to the tip of the finger 4. It will be appreciated that the cross-sectional contour of the finger stabilizing element 50 may become narrower and shallower in a substantially continuous slope. Alternatively, as illustrated herein in FIGS. 7 and 8, the cross-sectional contour may become narrower and shallower along a slope that varies along its length, which variance in said slope may be in stepped increments.

It will be appreciated that the contours of the upper and lower finger troughs are complimentary and that in the closed position, the end walls and side walls of the two troughs combine to form a substantially continuous surface that defines an interior volume that substantially corresponds to the shape of at least a portion of the end of a human finger. This is especially true of the end walls, which are carefully designed with a slope that corresponds to the shape of the finger tip.

Preferably, the finger stabilizing element 50 is configured from a material having flexibly soft malleable characteristics so as to sealingly engage the finger 4 and thereby at least lessen an amount of ambient light noise entering the device.

Figure 6:
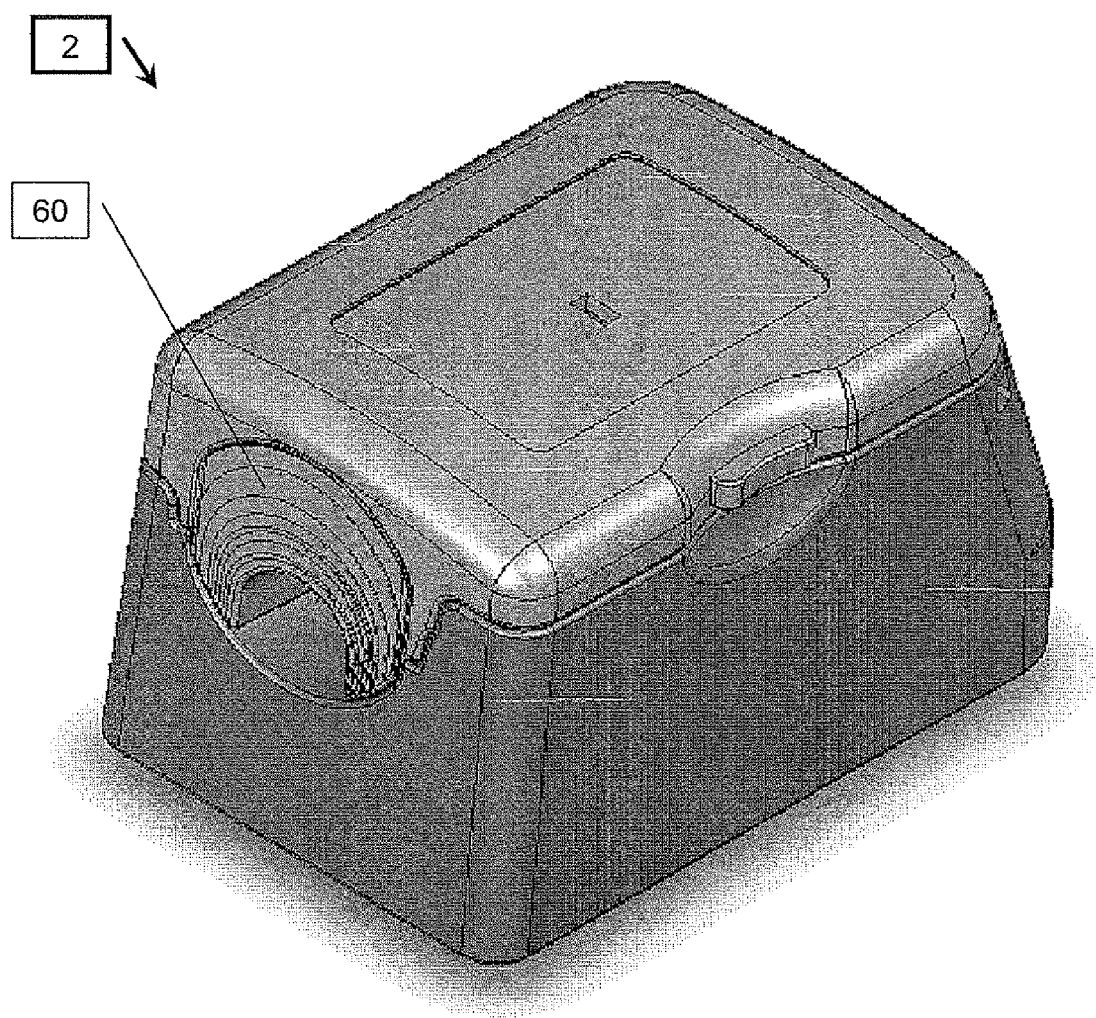
FIG. 6 is an isometric view of the embodiment of FIG. 1, showing multiple nesting finger stabilizing elements constructed and operational according to the teachings of the present invention.

It will be readily understood that the finger stabilizing element 50 may be implemented as a plurality of individual interchangeable elements each having a different sized finger engagement trough 54 corresponding to different sized human fingers 4. Alternatively, the finger stabilizing element 50 may be implemented as a plurality of nesting elements 60 each having a different sized said finger engagement trough corresponding to different sized human fingers. Such nesting elements 60 may be deployed such that the first surface of each nesting element is configured to attachably engage the second surface of the next element in the nesting sequence, as illustrated in FIG. 6.

Alternatively, the finger stabilizing element may be fabricated from material having very soft malleable gel like characteristics such that before deployment on finger 4 the finger stabilizing element may have a slightly convex contour, or areas that are convex and other areas that are concave. Yet, after deployment on finger 4 the finger stabilizing element reshapes so as to conform to the size and shape of the finger 4.

As illustrated in FIGS. 2 and 3, the device 2 includes at least one light source deployed on a sloped wall of a closed end of a lower finger-trough. The light source 80 is illustrated herein as an array of four lights, preferably LEDs, arranged in two rows of tow lights each. It should be noted that the number of lights and their arrangements may be varied and substantially any light source arrangement that is deployed on a sloping end wall is within the scope of the present invention. Further, the light emitted by the array of light sources 80 may be directed through at least one light source opening 120 as illustrated in FIGS. 12A and 12B.

Figure 12A:
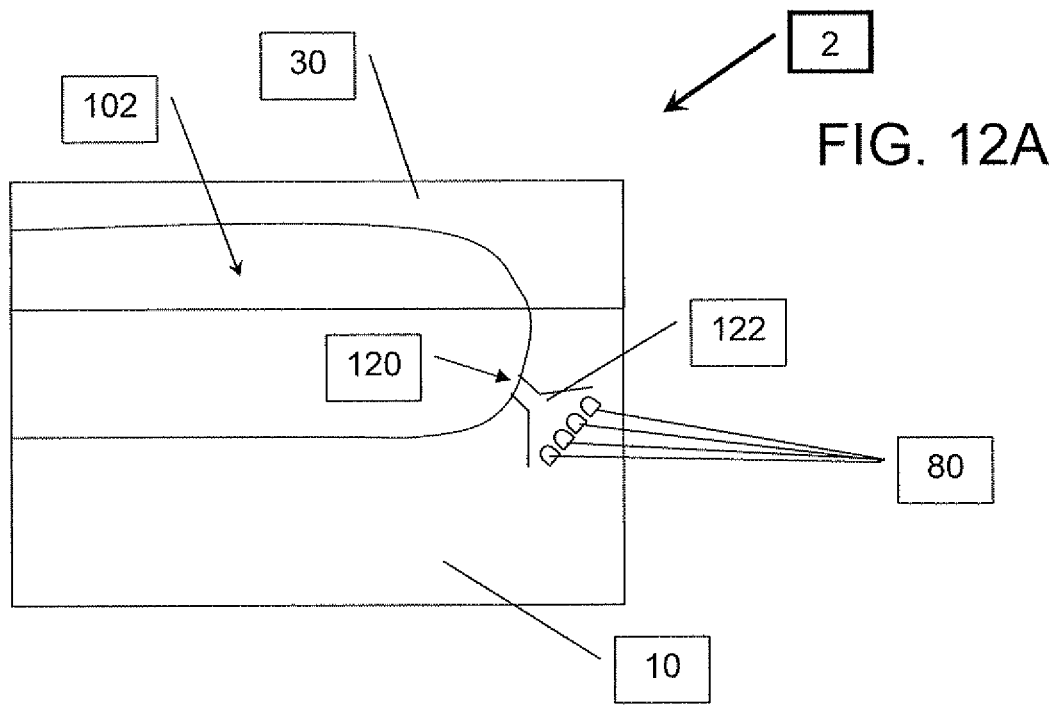
FIG. 12A is a schematic cross-sectional view of the embodiment of FIG. 9 illustrating a first embodiment of an array of light sources and a single light source opening.
Figure 12B:
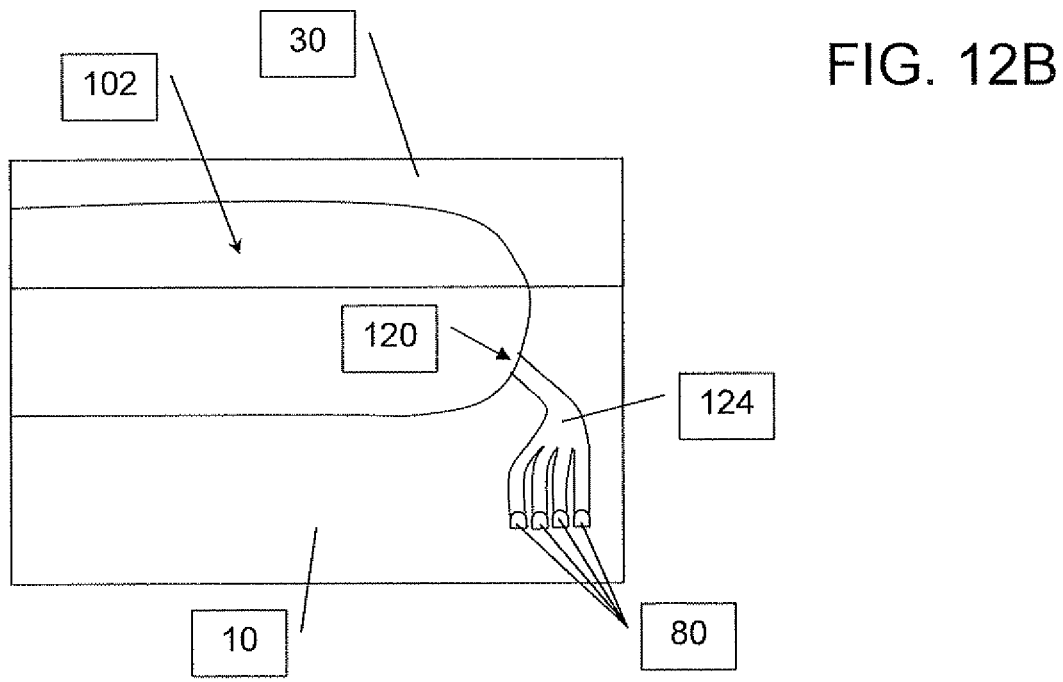
FIG. 12b is a schematic cross-sectional view of the embodiment of FIG. 9 illustrating a second embodiment of an array of light sources and a single light source opening.

FIG. 12A illustrates an embodiment in which the light emitted by the array of light sources 80 is directed to the light source opening 120 by walls 122. Such an arrangement requires that all of the light sources in the array be located within close proximity of the light source opening 120. FIG. 12B illustrates an embodiment in which the light emitted by the array of light sources 80 is directed to the light source opening 120 by a light tunnel arrangement 124. The light tunnel arrangement illustrated here for example only, includes individual light tunnels extending from each light source and combining into a single light tunnel that directs the light through light source opening 120. Such an arrangement does not require that all of the light sources in the array be located within close proximity of the light source opening 120 nor do they need to be in close proximity of each other. The light tunnel arrangement may be configured using fiber optics or other such technology.

The at least one light sensor opening 70 is configured in the bottom surface of the lower finger-trough 12. In such an arrangement, the light from the light source 80 enters the finger in an area of the lower portion of the tip of the finger 4 in the region just below the nail and at least a portion of the light exits the finger 4 in a area in the bottom of the finger before the first knuckle and thereby enters the light sensor opening 70.

As illustrated herein, the openings for the light source 80 and the light sensor opening 70 are each configured with a raised lip 82 and 72 respectively. The raised lips 82 and 72 circumscribe each of said openings for the light source 80 and the light sensor opening 70, so as to enhance contact with the surface of the finger by sealing engaging the finger 4 so as to assist in preventing ambient light, or light from the light source that did not enter the finger 4, from reaching the light sensor opening 70.

Figure 9:
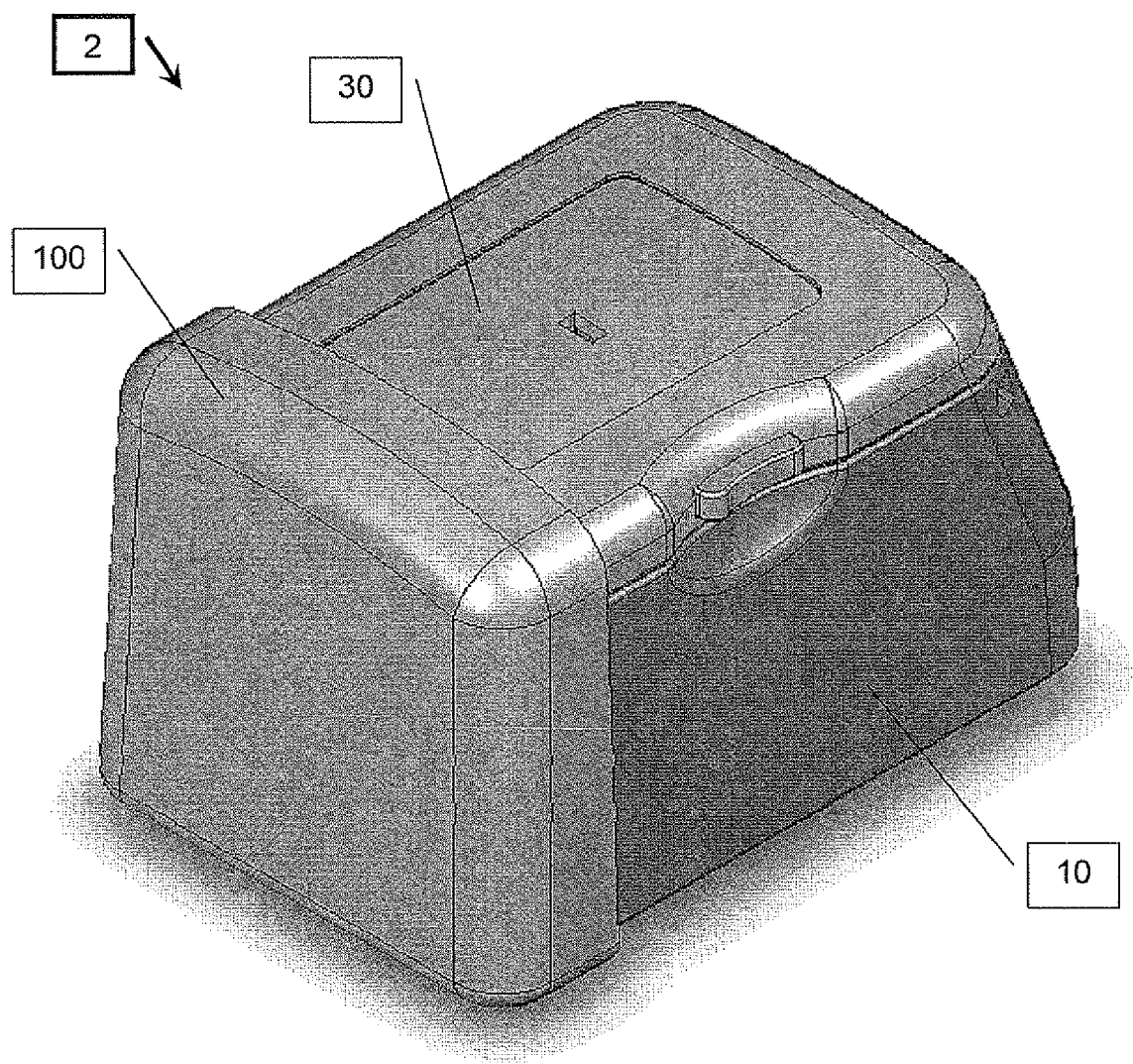
FIG. 9 is an isometric view of the embodiment of FIG. 1, showing an end cap constructed and operational according to the teachings of the present invention.
Figure 10:
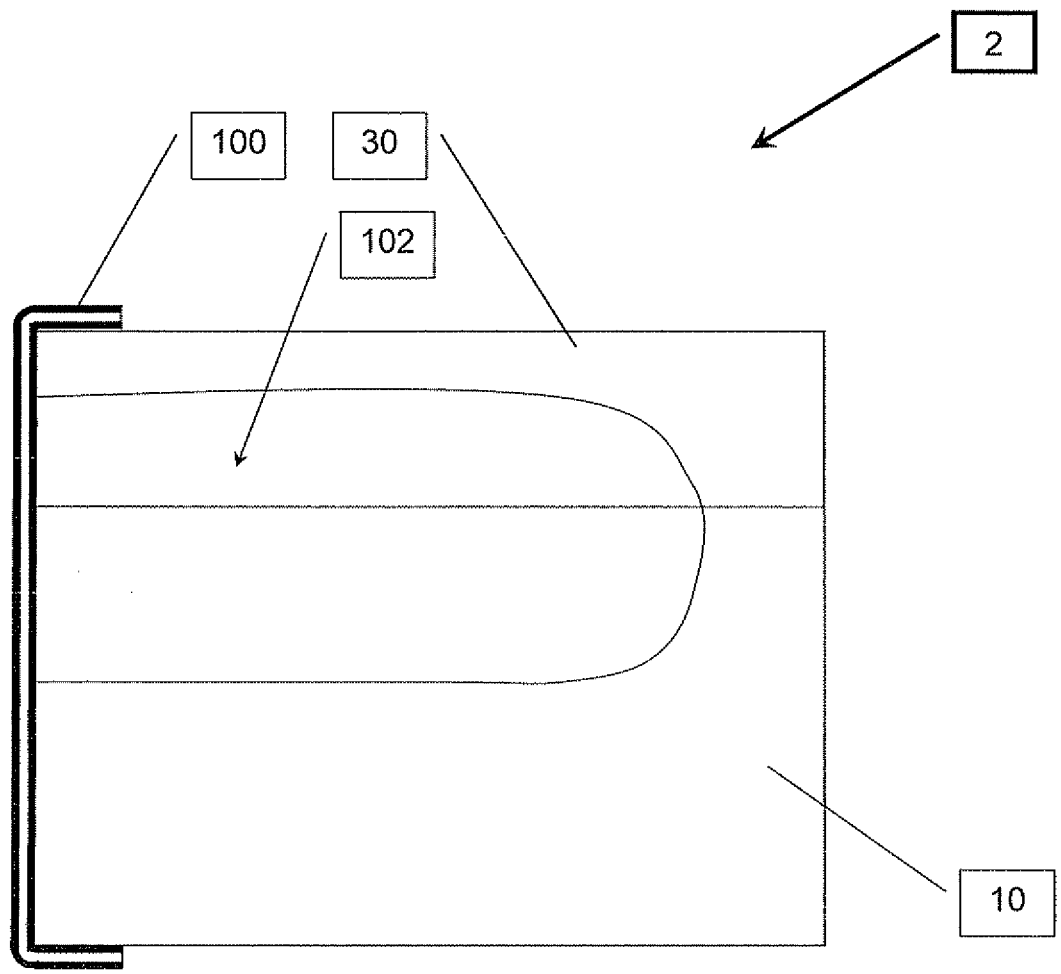
FIG. 10 is a schematic cross-sectional view of the embodiment of FIG. 9.
Figure 11:
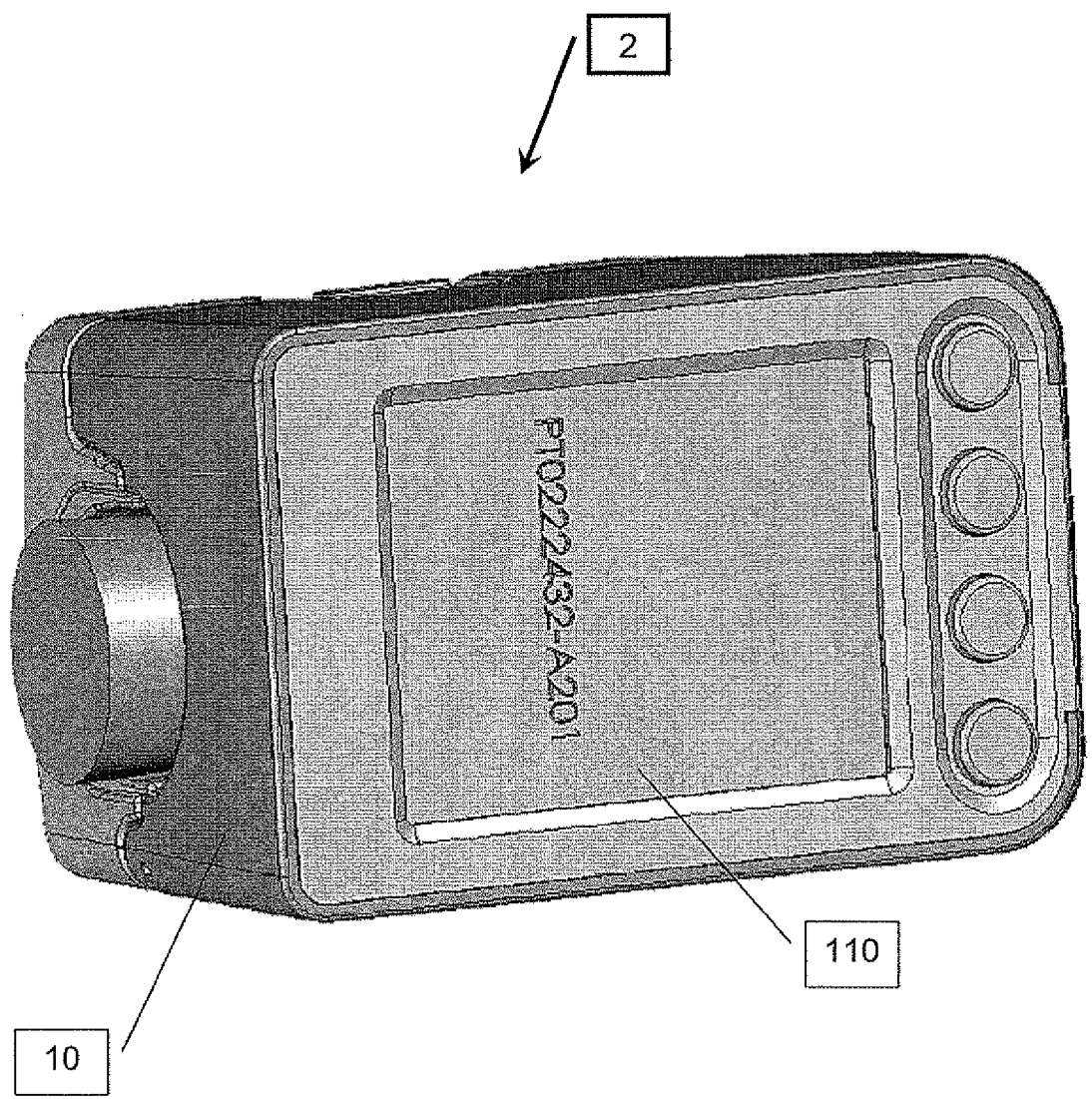
FIG. 11 is an isometric bottom view of the embodiment of FIG. 1 showing a readout display constructed and operational according to the teachings of the present invention.

As illustrated in FIGS. 9 and 10, an end cap 100 that is configured for deployment on the device 2 when the lid 30 is in a closed position is provided so as to substantially seal the open ends of the upper 32 and lower 12 finger-troughs such that ambient light is unable to enter an interior volume 102 defined by the lower 32 and upper 12 finger-troughs and the end cap 100, so as to enable calibration of the system. It will be readily understood that embodiment of an end cap 100 is solely for illustrative purposes and that substantially any suitable method or mechanism that prevents ambient light from entering the interior volume of the device 2 in the region of the light source opening and the light sensor opening and thereby enable calibration of the system, is within the scope of the present invention.

FIG. 10 illustrates the readout display unit 110 of the present invention deployed on an underside of the main housing 10. This unique design places the display 110 adjacent to the palm of the patient during use, as apposed to being adjacent to the top of the hand as is now standard in the art. Placement of the display adjacent to the palm makes it much easier for self reading of the display by the patient, which is beneficial and advantageous for home use of the device.

It will be appreciated that the above descriptions are intended only to serve as examples and that many other embodiments are possible within the spirit and the scope of the present invention.

What is claimed is:

1. A device for measuring blood and physiological characteristics, the device configured for deployment on a finger, the device comprising:
    (a) a main housing having a lower finger-trough configured to engage the bottom side of the finger, said lower finger-trough having an open end, a closed end and having cross-sectional contours that are complimentary to a bottom side of the finger;
    (b) a closeable lid having an upper finger-trough having an open end and a closed end that corresponds to said lower finger-trough, said lid being hingedly attached to said main housing and latchable in a closed position;
    (c) at least one finger stabilizing element configured for deployment in said upper finger-trough and configured to engage a top side of the finger;
    (d) at least one light source deployed on a sloped portion of said closed end of said lower finger-trough;
    (e) at least one light sensor opening configured in a bottom surface of said lower finger-trough; and
    (f) an end cap configured for deployment on the device when said lid is in a closed position so as to substantially close said open ends of said upper and lower finger-troughs.

2. The device of claim 1, further including:
    (g) a readout display unit deployed on said main housing so as to be adjacent to a palm of a hand of a patient during use.

3. A device for measuring blood and physiological characteristics, the device configured for deployment on a finger, the device comprising:
    (a) a main housing having a lower finger-trough configured to engage the bottom side of the finger, said lower finger-trough having an open end;
    (b) a closeable lid having an upper finger-trough having an open end that corresponds to said lower finger-trough; and
    (c) an end cap configured for deployment on the device when said lid is in a closed position;
wherein said end cap substantially seals said open ends of said upper and lower finger-troughs such that ambient light is unable to enter an interior volume defined by said lower and upper finger-troughs and said end cap.

4. The device of claim 3, further including a system for passing light through at least a portion of a human finger so as to measure blood and physiological characteristics, wherein said sealing of said open ends of said upper and lower finger-troughs enables calibration of said system.

\* \* \* \* \*